United States Patent [19]
Hartley et al.

[11] Patent Number: 5,635,513
[45] Date of Patent: Jun. 3, 1997

[54] 6-FLUORO-2,3,4,5-TETRAHYDRO-5-METHYL-2[(5-METHYL-1H-IMIDAZOL-4YL) METHYL]-1H-PYRIDO[4,3-B]INDOL-1-ONE METHANESULPHONATE

[75] Inventors: Peter L. Hartley, Stevenage; Tony G. Roberts, Ware, both of Great Britain; Leonard G. Whitesell, Research Triangle Park, N.C.

[73] Assignee: Glaxo Group Limited, Great Britain

[21] Appl. No.: 373,268

[22] PCT Filed: Jul. 29, 1993

[86] PCT No.: PCT/EP93/02014

§ 371 Date: Jan. 26, 1995

§ 102(e) Date: Jan. 26, 1995

[87] PCT Pub. No.: WO94/03452

PCT Pub. Date: Feb. 17, 1994

[30] Foreign Application Priority Data

Jul. 30, 1992 [GB] United Kingdom ............ 9216154

[51] Int. Cl.$^6$ ............ A61K 31/44; C07D 471/04
[52] U.S. Cl. ........................... 514/292; 546/86
[58] Field of Search ................... 514/292; 546/86

[56] References Cited

U.S. PATENT DOCUMENTS 5,183,820 2/1993 Coates .................... 514/292

*Primary Examiner*—C. Warren Ivy
*Assistant Examiner*—Evelyn Huang
*Attorney, Agent, or Firm*—Bacon & Thomas

[57] ABSTRACT

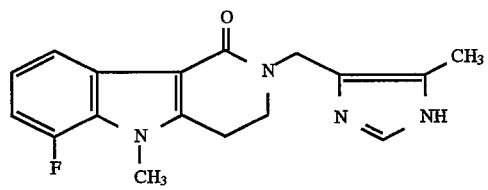

This invention relates to the novel salt 6-fluoro-2,3,4,5-tetrahydro-5-methyl-2[(5-methyl-1H-imidazol-4-yl) methyl]-1H-pyrido[4,3-b]indol-1-one methane sulphonate, to solvates of this salt, to pharmaceutical compositions containing it and to its use in medicine as 5-HT3 receptor antagonists.

16 Claims, No Drawings

6-FLUORO-2,3,4,5-TETRAHYDRO-5-METHYL-2[(5-METHYL-1H-IMIDAZOL-4YL) METHYL]-1H-PYRIDO[4,3-B]INDOL-1-ONE METHANESULPHONATE

This application is the national phase of PCT/EP93/02014 filed on Dec. 29, 1993.

This invention relates to a novel salt of 6-fluoro-2,3,4, 5-tetrahydro-5-methyl-2-[(5-methyl-1H-imidazol-4-yl)methyl]-1H-pyrido[4,3-b]indol-1-one, to solvates of this salt, to pharmaceutical compositions containing it and to its use in medicine.

6-Fluoro-2,3,4,5-tetrahydro-5-methyl-2-[(5-methyl-1H-imidazol-4-yl)methyl]-1H-pyrido[4,3-b]indol-1-one, which may be represented by the formula (I)

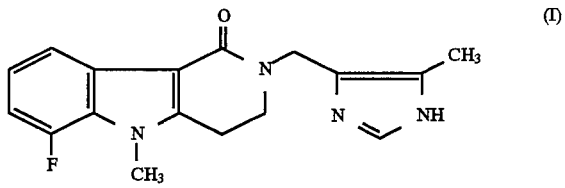

and its physiologically acceptable salts and solvates are described in European Patent Application publication No. 0353983. The compound of formula (I) is a potent and selective antagonist of 5-hydroxytryptamine (5-HT) at 5-HT$_3$ receptors and is useful in the treatment of, for example, emesis (i.e. nausea and vomiting), irritable bowel syndrome and gastrointestinal dysfunction such as dyspepsia. Physiologically acceptable salts of the compounds of formula (I) specifically disclosed in European Patent Application publication No. 0353983 are the maleate, benzoate and hydrochloride salts.

We have now found, surprisingly, that a novel salt of the compound of formula (I), and solvates, particularly hydrates of this salt, more particularly its dihydrate, is advantageous for the preparation of pharmaceutical compositions by virtue of its solubility and stability.

The present invention therefore provides in a first aspect 6-fluoro-2,3,4,5-tetrahydro-5-methyl-2-[(5-methyl-1H-imidazol-4-yl)methyl]-1H-pyrido-[4,3-b]indol-1-one methanesulphonate and physiologically acceptable solvates thereof.

Preferred solvates of the methanesulphonate salt of the compound of formula (I) are hydrates, in particular the dihydrate.

The preferred compound of the invention is 6-fluoro-2, 3,4,5-tetrahydro-5-methyl-2-[(5-methyl-1H-imidazol-4-yl)methyl]-1H-pyrido[4,3-b]indol-1-one methanesulphonate dihydrate.

The potent and selective antagonism of 5-HT at 5-HT$_3$ receptors by the compound of formula (I) has been demonstrated by its ability to inhibit 3-(5-methyl-1H-imidazol-4-yl)-1-[1-(methyl-t$_3$)-1H-indol-3-yl]-1-propanone binding in rat entorhinal cortex homogenates (following the general procedure described by G. Kilpatrick et al. in Nature, 1987, 330, 746).

In view of its 5-HT$_3$ antagonist activity, 6-fluoro-2,3,4, 5-tetrahydro-5-methyl-2-[(5-methyl-1H-imidazol-4yl)methyl]-1H-pyrido[4,3-b]indol-1-one methanesulphonate or a physiologically acceptable solvate is useful in the treatment of conditions ameliorated by antagonism of 5-HT at 5-HT$_3$ receptors, such as emesis (i.e. nausea and vomiting), particularly that associated with cancer chemotherapy and radiotherapy, that occurring post operatively, and also that induced by opioids; cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Impairment; psychotic disorders, such as schizophrenia and mania; anxiety disorders, including panic disorder, agoraphobia, social phobia, simple phobia, obsessive compulsive disorders, post traumatic stress disorder, mixed anxiety and depression, and generalized anxiety disorder; irritable bowel syndrome; gastric stasis; symptoms of gastrointestinal dysfunction such as occur with dyspepsia, peptic ulcer, reflux oesophagitis and flatulence; migraine; obesity and conditions such as bulimia; pain; dependency on drugs and substances of abuse; and depression.

There is also provided as a further aspect of the invention 6-fluoro-2,3,4,5-tetrahydro-5-methyl-2-[(5-methyl-1H-imidazol-4-yl)methyl]-1H-pyrido[4,3-b]indol-1-one methanesulphonate or a physiologically acceptable solvate thereof for use in therapy, in particular in human medicine. It will be appreciated that use in therapy embraces but is not necessarily limited to use of 6-fluoro-2,3,4,5-tetrahydro-5-methyl-2-[(5-methyl-1H-imidazol-4-yl)methyl]-1H-pyrido[4,3-b]indol-1-one methanesulphonate or a physiologically acceptable solvate thereof as an active therapeutic substance.

It will be appreciated that reference to treatment is intended to include prophylaxis as well as the alleviation of established symptoms.

In an alternative aspect of the invention there is provided the use of 6-fluoro-2,3,4,5-tetrahydro-5-methyl-2-[(5-methyl-1H-imidazol-4-yl)methyl]-1H-pyrido[4,3-b]indol-1-one methanesulphonate or a physiologically acceptable solvate thereof in the preparation of a medicament for use in the treatment of a human or animal subject suffering from a condition ameliorated by antagonism of 5-HT at 5-HT$_3$ receptors.

According to another aspect of the invention there is provided a method of treating a human or animal subject suffering from a condition ameliorated by antagonism of 5-HT at 5-HT$_3$ receptors, which method comprises administering to said subject an effective amount of 6-fluoro-2,3, 4,5-tetrahydro-5-methyl-2-[(5-methyl-1H-imidazol-4-yl) methyl]-1H-pyrido[4,3-b]indol-1-one methanesulphonate or a physiologically acceptable solvate thereof.

The anhydrous methanesulphonate salt of the compound of formula (I) is also of use as an intermediate in the preparation of solvates thereof.

While it is possible that, for use in therapy, the compounds of the invention may be administered as the raw chemical it is preferable to present combinations as a pharmaceutical composition.

There is thus provided in a further aspect of the invention a pharmaceutical composition comprising 6-fluoro-2,3,4,5-tetrahydro-5-methyl-2-[(5-methyl-1H-imidazol-4-yl)methyl]-1H-pyrido[4,3-b]indol-1-one methanesulphonate or a physiologically acceptable solvate, for example a hydrate, such as a dihydrate thereof as active ingredient, together with a physiologically acceptable carrier, for use in human or veterinary medicine, and formulated for administration by any convenient route.

Such compositions may be formulated in conventional manner using one or more physiologically acceptable carriers and/or excipients.

Thus the compound according to the invention or a physiologically acceptable solvate thereof may be formulated for oral, buccal, parenteral, transdermal or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. Avicel PH102, lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

Tablets for oral administration may be suitably formulated to provide very fast release of the active compound, for example by formulation as a lyophilised tablet.

For buccal administration the compositions may take the form of tablets or lozenges formulated in conventional manner.

The compound of the invention or a physiologically acceptable solvate thereof may be formulated for parenteral administration by bolus injection or continuous infusion. Formulations for injection may be presented in unit dosage form e.g. in ampoules, vials, syringes or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

A preferred composition for injection is a solution, particularly an aqueous solution. Such solutions may additionally contain other excipients, such as preservatives (for example methyl p-hydroxybenzoate or propyl p-hydroxybenzoate), buffering agents or isotonicity-adjusting agents (for example dextrose, sodium chloride or mannitol).

Preferably solutions according to the invention will be sterile, free from particulates and free from preservatives. Sterile formulations may be prepared by methods well known in the art, for example by aseptic manufacture or sterilisation of bulk products.

Aqueous solutions of the methanesulphonate dihydrate of the present invention adapted for injection will have a pH in the range 2 to 7. Most preferably the pH of aqueous solutions of the methanesulphonate dihydrate of the present invention will be 3 to 5, such as 3.9 to 4.1. Adjustment of the pH of aqueous solutions of the methanesulphonate dihydrate of the compound of formula (I) to within the desired range is conveniently effected by addition of an acid and/or base. Suitable acids include inorganic acids, for example hydrochloric acid; suitable bases include inorganic bases, such as alkali metal hydroxides, for example sodium hydroxide.

For transdermal administration the compounds of the invention may be formulated as creams, gels, ointments or lotions or as transdermal patches. Such compositions may, for example, be formulated with an aqueous or oily base with the addition of suitable thickening, gelling, emulsifying, stabilising, dispersing, suspending, and/or colouring agents.

The compound of the invention or a physiologically acceptable solvate thereof may also be formulated in rectal compositions such as suppositories or retention enemas, e.g. containing conventional suppository bases such as cocoa butter or other glycerides.

In addition to the formulations described previously, the compound of the invention or a physiologically acceptable solvate thereof may also be formulated as depot preparations. Such long acting formulations may be administered by implantation (for example subcutaneously or intramuscularly) or by intramuscular injection. Thus, for example, the compound of the invention or a physiologically acceptable solvate thereof may be formulated with suitable polymeric or hydrophobic materials (for example as an emulsion in an acceptable oil) or ion exchange resins, or as sparingly soluble derivatives.

For administration by inhalation the compound according to the invention or a physiologically acceptable solvate thereof is conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of the compound of the invention or a physiologically acceptable solvate thereof and a suitable powder base such as lactose or starch.

For intranasal administration, the compound according to the invention or a physiologically acceptable solvate thereof may be formulated as solutions for administration via a suitable metered or unit dose device or alternatively as a powder mix with a suitable carrier for administration using a suitable delivery device.

The compound of the invention or a physiologically acceptable solvate thereof may also be administered in combination with other therapeutic agents. Thus, for example, in the treatment of gastric stasis, symptoms of gastrointestinal dysfunction and emesis (i.e. nausea and vomiting), the compound of the invention or a physiologically acceptable salt thereof may be administered in combination with antisecretory agents such as histamine $H_2$-receptor antagonists (e.g. ranitidine, sufotidine, cimetidine, famotidine, nizatidine or roxatidine) or H+K+ ATPase inhibitors (e.g. omeprazole). In the treatment of emesis (i.e. nausea and vomiting), the compound of the invention or a physiologically acceptable solvate thereof may also be administered in combination with dexamethasone or a cyclo-oxygenase inhibitor such as piroxicam.

A proposed dose of the compounds of the invention for administration to man (of approximately 70 kg body weight) is 0.001 to 100mg, preferably 0.01 to 50 mg, more preferably 0.1 to 20 mg of the active ingredient per unit dose expressed as the weight of free base, which could be administered, for example, 1 to 4 times per day. It will be appreciated that it may be necessary to make routine variations to the dosage, depending on the age and condition of the patient and the nature of the condition to be treated, and will be at the ultimate discretion of the attendant physician. The dosage will also depend on the route of administration.

The compound of the invention and physiologically acceptable solvates thereof may be prepared by the general methods outlined hereinafter.

According to one general process (A), the compound of the invention or a solvate thereof may be prepared by reaction of 6-fluoro-2,3,4,5-tetrahydro-5-methyl-2-[(5-methyl-1H-imidazol-4-yl)methyl]- 1H- pyrido[4,3-b]indol-1-one or a solvate thereof with methanesulphonic acid. The reaction may be carried out in the presence of a solvent, such as an alcohol (for example Industrial Methylated Spirits (IMS) or ethanol), or an aqueous alcohol (for example aqueous propan-1-ol) and preferably at elevated temperature (for example reflux).

According to one embodiment of process (A), where the compound of the invention is desired in anhydrous form, it is preferably prepared by admixture of the free base and methanesulphonic acid in IMS, at reflux. Preferably, the free base of the compound of the invention is recrystallised from methanol prior to use as a starting material.

According to another embodiment of process (A), where the compound of the invention is desired in hydrated form, in particular as its dihydrate, it is preferably prepared by admixture of the free base and methanesulphonic acid in aqueous propan-1-ol at a temperature preferably in the range $20°$ C.–$90°$ C. Most preferably the reaction will be carried out at a temperature of between $40°$ C.–$80°$ C., such as $60°$–$70°$ C.

According to another general process (B), a solvate of the compound of the invention may be prepared by reaction of the compound of the invention in anhydrous form or a solvate thereof with an appropriate solvent, if necessary at elevated temperature.

For example the hydrate, particularly the dihydrate of the compound of the invention may be prepared by reaction of the compound of the invention or a solvate thereof with water, if necessary at elevated temperature.

Such processes (A), and (B) form further aspects of the invention.

The following non-limiting examples further illustrate the invention.

INTERMEDIATE 1

6-Fluoro-2,3,4,5-tetrahydro-5-methyl-2-[(5-methyl-1H- imidazol-4-yl)-methyl]- 1H- pyrido[4,3-b] indol-1-one 6-Fluoro-2,3,4,5-tetrahydro-5-methyl-2-[(5-methyl- 1H-imidazol-4-yl)methyl]-1H-pyrido[4,3-b]indol-1-one was dissolved in methanol (30 ml) at reflux. Water (15 ml) was added to the hot solution at $60°$ maintaining a clear solution. The solution was cooled for 1 hour at $0°$ and the solid was filtered off, washed with methanol:water (2:1, 15 ml) at room temperature. The solid was dried in vacuo at $60°$ to constant weight to give a second polymorphic form of the title compound as a white solid (3.7 g).

IR (Nujol Mull): 3208 $cm^{-1}$, 1633 $cm^{-1}$

Water Analysis Found: 0.5% w/w

EXAMPLE 1

6-Fluoro-2,3,4,5-tetrahydro-5-methyl-2-[(5-methyl-1H- imidazol-4-yl)methyl]- 1H- pyrido[4,3-b]indol-1-one methanesulphonate 6-Fluoro-2,3,4,5-tetrahydro-5-methyl-2-[(5-methyl- 1H-imidazol-4-yl)methyl]-1H-pyrido[4,3-b]indol-1-one (224.9 g) was suspended in IMS (1125 ml) and heated to reflux. A solution of methanesulphonic acid (69.2 g) in IMS (675 ml) was added with stirring over 15 minutes. The mixture was subsequently allowed to cool over 3 hours, then seeded and left overnight at ambient temperature before being cooled to $4°$ C. for 5 hours, with stirring. The mixture was filtered, the solid washed with cold IMS (2×450 ml), and then dried between $40°$ and $76°$ C. in vacuo to give the title compound (226 g) as a crystalline solid.

Water Analysis Found: 0.8% w/w=0.20 mol $H_2O$

Analysis Found: C, 52.5; H, 5.2; N, 13.5; $C_{17}H_{17}FN_4O.CH_4O_3S$ Requires: C, 52.9; H, 5.2; N, 13.7%.

EXAMPLE 2

6-Fluoro-2,3,4,5-tetrahydro-5-methyl-2-[(5-methyl-1H- imidazol-4-yl)methyl]- 1H- pyrido[4,3-b]indol-1-one methanesulphonate dihydrate To 6-fluoro-2,3,4,5-tetrahydro-5-methyl-2-[(5-methyl-1H- imidazol-4-yl)methyl]-1H-pyrido[4,3-b]indol-1-one methanesulphonate (33.0 g) was added water (112 ml) and the mixture heated to $45°$ C. to give a clear yellow solution. This solution was allowed to reach ambient temperature, then cooled to $10°$ C., whereupon the mixture was filtered and the solid washed with water (20 ml, at $10°$ C.). The solid was dried at $48°$ C. in vacuo for 16 hours to give the title compound (20.3 g).

Water Analysis Found: 8.2% w/w=2.02 mol $H_2O$

Analysis Found: C, 48.8; H, 5.7; N, 12.6; S, 7.2; $C_{17}H_{17}FN_4O.CH_4O_3S.2H_2O$ Requires: C, 48.6; H, 5.7; N, 12.6; S, 7.2%

EXAMPLE 3

6-Fluoro-2,3,4,5-tetrahydro-5-methyl-2-[(5-methyl-1H- imidazol-4-yl)methyl]- 1H- pyrido[4,3-b]indol-1-one methanesulphonate dihydrate Water (0.29 l) and methanesulphonic acid (0.23 l) was added to a suspension of 6-fluoro-2,3,4,5-tetrahydro-5-methyl-2-[(5-methyl-1H-imidazol-4-yl)methyl]- 1H- pyrido [4,3-b]indol-1-one (1.04 kg) in propan-1-ol (7.4 l). The mixture was heated to about $65°$ C. to give a clear solution, which was filtered, and the filter rinsed with propan-1-ol. The combined filtrate and wash were cooled to about $15°$ C. and diisopropyl ether (7.9 l) was added to the resulting suspension. The mixture was cooled to $5°$ C., and the solid isolated by filtration, washed with diisopropyl ether:propan-1-ol (3:1, 2×1.8 l) and diisopropyl ether (2×2 l) and finally dried in vacuo at about $35°$ C. to yield the title compound (1.39 kg).

The analysis and water analysis for this material were consistent with those obtained for the product of Example 2.

EXAMPLE 4

STERILE FORMULATION

|  | mg/ml |
| --- | --- |
| Compound of formula (I), methanesulphonate dihydrate | 1.42 mg |
| Dextrose Monohydrate USP | 55.00 mg |
| Hydrochloric Acid NF | adjust to pH4 |
| Sodium Hydroxide NF | adjust to pH4 |
| Water for Injection USP | qs to 1 ml |

The compound of formula (I) methanesulphonate dihydrate was dissolved in water and the solution made up to approximately 85% of volume. Dextrose Monohydrate USP was added and the pH of the solution was adjusted to 4.0 using hydrochloric acid and/or sodium hydroxide. The solution was made up to final volume with water and the pH remeasured and adjusted if necessary, to provide 1 mg/ml of the compound of formula (I).

The solution may be packaged for injection, for example by filling and sealing in ampoules, vials or syringes. The ampoules, vials or syringes may be aseptically filled and/or terminally sterilised by, for example, autoclaving at 121° C.

Further sterile formulations were prepared, in a similar manner, containing 0.142 mg and 14.23 mg of the compound of formula (I) methanesulphonate dihydrate, so as to provide 0.1 mg/ml and 10 mg/ml respectively of the compound of formula (I)

TABLETS FOR ORAL ADMINISTRATION

Tablets may be prepared by the normal methods such as direct compression or wet granulation.

The tablets may be film coated with suitable film forming materials, such as Opadry White, type YS-1-7027, using standard techniques. Alternatively the tablets may be sugar coated.

EXAMPLE 5

Direct Compression

| Tablet | mg/Tablet |
|---|---|
| Compound of formula (I), methanesulphonate dihydrate | 0.71 mg |
| Magnesium Stearate | 0.75 mg |
| Avicel PH102 | qs 150.00 mg |

The compound of formula (I) methanesulphonate dihydrate is passed through a 30 mesh sieve and blended with Avicel PH102 and magnesium stearate. The resultant mix is compressed into tablets using a suitable tablet machine fitted with 9/32" diameter punches.

Tablets of other strengths, containing for example 0.142, 2.85 or 11.38 mg/tablet of the compound of formula (I) methanesulphonate dihydrate, may be prepared in a similar manner, so as to provide 0.1, 2 or 8 mg/tablet of the compound of formula (I).

EXAMPLE 6

WET GRANULATION

A formulation as described in Example 5 may be used. The compound of formula (I) methanesulphonate dihydrate is dissolved in a suitable volume of granulating solution (purified water or 10% PVP K29/32 in water). After drying, the granules are screened, for example through 20 mesh screen, and blended with magnesium stearate. The granules are then compressed into tablets as described in Example 5.

Tablets of other strengths, such as those described in Example 5, may be prepared in a similar manner.

EXAMPLE 7

SUPPOSITORY

| | |
|---|---|
| Compound of formula (I), methanesulphonate dihydrate | 14.23 mg |

-continued

| | |
|---|---|
| Witepsol W32, hard fat | 2000 mg |
| qs | |

Blend micronized drug in a portion of the melted Witepsol W32 at approximately 36° C. for approximately 15 minutes in a high speed mixer. Incorporate the homogenized slurry into the remaining portion of the melted Witepsol W32 and blend at approximately 36° C. until satisfactory dispersion is achieved. Fill moulds with 2000 mg formulation, to provide 10 mg/suppository of compound of formula (I).

EXAMPLE 8

CAPSULE

| | mg/capsule |
|---|---|
| Compound of formula (I), methanesulphonate dihydrate | 14.23 mg |
| Polyethylene glycol | 92.89 mg |
| Propylene glycol | qs 200 mg |

Blend together polyethylene glycol and propylene glycol using heat as necessary. Stir until homogeneous. Add micronised compound of formula (I) methanesulphonate dihydrate to blend. Mix until homogenous. Fill into an appropriate gelatin mass to give soft gelatin capsules containing 200 mg of the formulation, to provide 10 mg/capsule of compound of formula (I).

EXAMPLE 9

ORAL SYRUP

| | mg/ml |
|---|---|
| Compound of formula (I), methanesulphonate dihydrate | 2.85 mg |
| Sucrose | 200 mg |
| Methylparaben | 1.2 mg |
| Propylparaben | 0.15 mg |
| Flavouring | 1.5 mg |
| Citric Acid | 0.1 mg |
| Purified Water | qs 1 ml |

Dissolve the parabens in a small portion of the water that has been heated to approximately 90° C. Add the paraben solution to a large portion of the remaining water with mixing. Add and dissolve the other components. Bring the formulation to final volume and mix until homogenous. Fill the formulation into a containing, such as a unit dose cup or a bottle for multiple-dose use, to provide 2 mg/5 ml.

EXAMPLE 10

TRANSDERMAL SYSTEM

| | |
|---|---|
| Compound of formula (I), methanesulphonate dihydrate | 5% (of compound of formula (I)) |
| Silicone fluid | 90% |
| Colloidal silicone dioxide | 5% |

The silicone fluid and drug are mixed together and the colloidal silicone dioxide is added to increase the viscosity. The material is then dosed into a subsequently heat sealed polymeric laminate comprised of the following: polyester release liner, skin contact adhesive composed of silicone or acrylic polymers, a control membrane which is a polyolefin (e.g. polyethylene or polyvinyl acetate) or polyurethane, and an impermeable backing membrane of a polyester multilaminate.

EXAMPLE 11

LYOPHILIZED PRODUCT

| | | |
|---|---|---|
| Compound of formula (I), methanesulphonate dihydrate | 14.23 mg | |
| Mannitol | 50.00 mg | |
| Citrate buffer | 0.75 mg | |
| Water for injection | qs | 1 ml |

Dissolve components in a portion of the water for injection. Make formulation up to final volume and mix until homogenous. Filter formulation through a sterilising filter and fill into glass vials. Lyophilize and seal vials. Reconstitute with appropriate solvent prior to use.

We claim:

1. 6-Fluoro-2,3,4,5-tetrahydro-5-methyl-2-[(5-methyl-1H- imidazol-4-yl)methyl]-1H-pyrido[4,3-b]indol-1-one methanesulphonate, and solvates thereof.

2. 6-Fluoro-2,3,4,5-tetrahydro-5-methyl-2-[(5-methyl-1H- imidazol-4-yl)methyl]-1H-pyrido[4,3-b]indol-1-one methanesulphonate in the form of a hydrate.

3. A pharmaceutical composition comprising 6-fluoro-2,3,4,5-tetrahydro-5-methyl-2-[(5-methyl- 1H- imidazol-4-yl)methyl]-1H-pyrido[4,3-b]indol-1-one methanesulphonate or a solvate thereof as defined in claim 1 together with at least one physiologically acceptable carrier or excipient.

4. A pharmaceutical composition according to claim 3 in a form adapted for oral or parenteral administration.

5. 6-Fluoro-2,3,4,5-tetrahydro-5-methyl-2-[(5-methyl-1H- imidazol-4-yl)methyl]-1H-pyrido[4,3-b]indol-1-one methanesulphonate or a solvate thereof as defined in claim 1 for use in therapy.

6. A method of treating a human or animal subject suffering from a condition ameliorated by antagonism of 5-HT at 5-$HT_3$ receptors, which method comprises administering to said subject an effective amount of 6-fluoro-2,3,4,5-tetrahydro-5-methyl-2-[(5-methyl- 1H- imidazol-4-yl)methyl]-1H-pyrido[4,3-b]indol-1-one methanesulphonate or a solvate thereof as defined in claim 1.

7. A compound according to claim 2 which is 6-fluoro-2,3,4,5-tetrahydro-5-methyl-2-[(5-methyl- 1H- imidazol-4-yl)methyl]-1H-pyrido[4,3-b]indol-1-one methanesulphonate dihydrate.

8. A pharmaceutical composition comprising a hydrate of 6-fluoro-2,3,4,5-tetrahydro-5-methyl-2-[(5-methyl- 1H- imidazol-4-yl)methyl]-1H-pyrido[4,3-b]indol-1-one methanesulphonate as claimed in claim 2 together with at least one physiologically acceptable carrier or excipient.

9. A pharmaceutical composition comprising 6-fluoro-2,3,4,5-tetrahydro-5-methyl-2-[(5-methyl- 1H- imidazol-4-yl)methyl]-1H-pyrido[4,3-b]indol-1-one methanesulphonate dihydrate as claimed in claim 7 together with at least one physiologically acceptable carrier or excipient.

10. A pharmaceutical composition as claimed in claim 8 adapted for oral or parenteral administration.

11. A pharmaceutical composition as claimed in claim 9 adapted for oral or parenteral administration.

12. A method of treating a human or animal subject suffering from a condition ameliorated by antagonism of 5-HT at 5-$HT_3$ receptors, which method comprises administering to said subject an effective amount of a hydrate of 6-fluoro-2,3,4,5-tetrahydro-5-methyl-2-[(5-methyl- 1H- imidazol-4-yl)methyl]-1H-pyrido[4,3-b]indol-1-one methanesulphonate as claimed in claim 2.

13. A method of treating a human or animal subject suffering from a condition ameliorated by antagonism of 5-HT at 5-$HT_3$ receptors, which method comprises administering to said subject an effective amount of 6-fluoro-2,3,4,5-tetrahydro-5-methyl-2-[(5-methyl- 1H- imidazol-4-yl)methyl]-1H-pyrido[4,3-b]indol-1-one methanesulphonate dihydrate as claimed in claim 7.

14. A method of treating a human or animal subject suffering from nausea or vomiting which comprises administering to said subject an effective amount of 6-fluoro-2,3,4,5-tetrahydro-5-methyl-2-[(5-methyl- 1H- imidazol-4-yl)methyl]-1H-pyrido[4,3-b]indol-1-one methanesulphonate or a solvate thereof as defined in claim 1.

15. A method of treating a human or animal subject suffering from nausea or vomiting which comprises administering to said subject an effective amount of a hydrate of 6-fluoro-2,3,4,5-tetrahydro-5-methyl-2-[(5-methyl- 1H- imidazol-4-yl)methyl]-1H-pyrido [4,3-b]indol-1-one methanesulphonate as claimed in claim 2.

16. A method of treating a human or animal subject suffering from nausea or vomiting which comprises administering to said subject an effective amount of 6-fluoro-2,3,4,5-tetrahydro-5-methyl-2-[(5-methyl- 1H- imidazol-4-yl)methyl]-1H-pyrido[4,3-b]indol-1-one methanesulphonate dihydrate as claimed in claim 7.

\* \* \* \* \*